United States Patent [19]

Sears

[11] E Re. 31,609

[45] Reissued Jun. 19, 1984

[54] METHOD OF PREPARING A CONTROLLED-RELEASE PHARMACEUTICAL PREPARATION, AND RESULTING COMPOSITION

[75] Inventor: Barry D. Sears, Marblehead, Mass.

[73] Assignee: Lipid Specialties, Inc., Cambridge, Mass.

[21] Appl. No.: 103,463

[22] Filed: Dec. 14, 1979

Related U.S. Patent Documents

Reissue of:

[64] Patent No.: 4,145,410
Issued: Mar. 20, 1979
Appl. No.: 807,373
Filed: Jun. 17, 1977

U.S. Applications:

[63] Continuation-in-part of Ser. No. 731,132, Oct. 12, 1976, Pat. No. 4,086,257, Ser. No. 770,290, Feb. 22, 1977, Pat. No. 4,097,503, and Ser. No. 770,407, Feb. 22, 1977, Pat. No. 4,097,502.

[51] Int. Cl.[3] ..... A61K 9/52; B01J 13/02

[52] U.S. Cl. ..... 424/19; 424/25; 424/36; 424/178; 427/213.3

[58] Field of Search ..... 252/316; 424/19, 25, 424/36

[56] References Cited

U.S. PATENT DOCUMENTS

| | | | |
|---|---|---|---|
| Re. 30,748 | 9/1981 | Sears | 260/403 |
| 4,016,100 | 4/1977 | Suzuki et al. | 252/316 |
| 4,159,988 | 7/1979 | Eibl et al. | 260/340.9 R |

OTHER PUBLICATIONS

Gregoriadis: "The Carrier Potential of Liposomes in Biology and Medicine," New England J. Med. 295, 704–710, Sep. 23, 1976.

*Primary Examiner*—Richard D. Lovering
*Attorney, Agent, or Firm*—Richard P. Crowley

[57] ABSTRACT

A method of preparing a controlled-release pharmaceutical compound for oral administration, which pharmaceutical compound is subject to enzymatic hydrolysis on oral administration, which method comprises encapsulating the pharmaceutical compound with a synthetic phosphatidyl compound having a modified polarhead moiety which increases the resistance of the phosphatidyl compound to phospholipase C hydrolysis.

10 Claims, 1 Drawing Figure

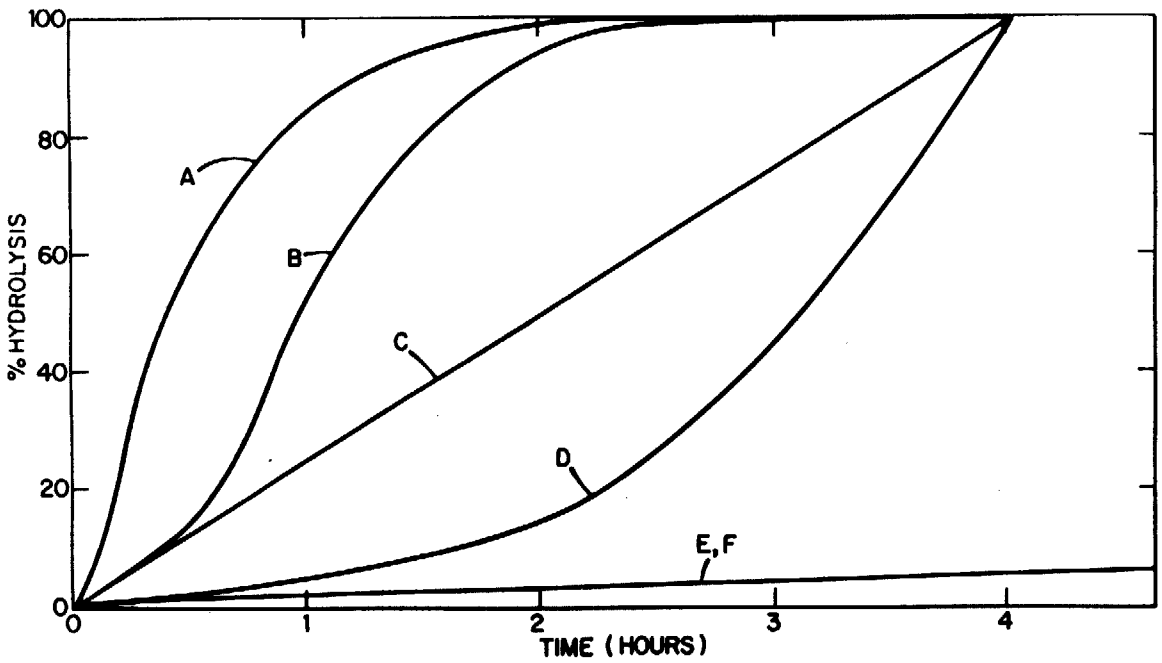
% HYDROLYSIS
100
80
60
40
20
0
0
1
2
3
4
TIME (HOURS)
A
B
C
D
E,F

METHOD OF PREPARING A CONTROLLED-RELEASE PHARMACEUTICAL PREPARATION, AND RESULTING COMPOSITION

Matter enclosed in heavy brackets [ ] appears in the original patent but forms no part of this reissue specification; matter printed in italics indicates the additions made by reissue.

REFERENCE TO PRIOR APPLICATIONS

This application is a continuation-in-part of my copending patent applications U.S. Ser. No. 731,132, filed Oct. 12, 1976 (now U.S. Pat. No. 4,086,257, issued Apr. 25, 1978); U.S. Ser. No. 770,290, filed Feb. 22, 1977 (now U.S. Pat. No. 4,097,503, issued June 27, 1978); and U.S. Ser. No. 770,407, filed Feb. 22, 1977 (now U.S. Pat. No. 4,097,502, issued June 27, 1978), all hereby incorporated by reference.

BACKGROUND OF THE INVENTION

Phospholipids are amipathic compounds that tend to self-associate in aqueous systems to form micelles with a hydrophobic interior and hydrophilic exterior. Two types of structures can be formed by phospholipids. One type is vesicles in which a phospholipid bilayer encloses an aqueous internal space. Since the phospholipid bilayer acts as a barrier between the aqueous internal space and the outer aqueous environment, various water-soluble compounds can be sequestered in the internal aqueous space. As a result, this particular structure has been used as a drug-delivery system (see G. Gregoriadis, New England J. Med. 295 704 (1976) and G. Gregoriadis, New England J. Med. 295 765 (1976)).

Another type of system that phospholipids can form is microemulsions in which a highly water-insoluble substance, such as cholesterols, cholesterol esters and derivatives, or triglycerides, forms an inner core surrounded by an outer monolayer of phospholipid (see L. Shorr et al., Biophys. J. 17 81a (1977)). Since the interior of these structures is hydrophobic, compounds which are nonpolar can be sequestered in the interior core of these microemulsion structures.

While both of such structures offer potentially new methods of drug delivery, much of this potential is modulated by the fact that both drug-delivery systems only have activity if directly injected into the bloodstream. Usually oral administration is not possible, since the phospholipids used would be hydrolyzed in the stomach, and hence any associated drug would be released, in whole or in part, in the stomach, and would be hydrolyzed by itself or at least exhibit a decrease in the maximal effectiveness of the drug. On the other hand, if the phospholipids could be altered in such a manner to resist hydrolysis, then oral administration of such drug-delivery systems is possible, as the delivery system would be able to pass through the stomach intact and then be absorbed by the gut.

The major enzymes responsible for the hydrolysis of phospholipids in mammals are phospholipase A and phospholipase C.

Phospholipase $A_2$, which hydrolyzes the acyl chains of phospholipids, is maximally active at the transition temperature when the phospholipids are melting into a liquid crystalline state (see J.A.F. Op Den Kamp et al., Biochem. Biophys. Acta 406 169 (1975)). At temperatures in which the phospholipid is in the gel state, the enzyme is relatively inactive. Furthermore, if the acyl linkages to the glycerol backbone of the phospolipids are replaced by ether linkages, then the phospholipid is totally inactive. Thus, phospholipase $A_2$ hydrolysis can be prevented rather easily.

Phospholipase C hydrolyzes the polar moiety of the phospholipid. Therefore, the physical state of the acyl chains has little bearing on the hydrolysis of the polar-head group. Thus, it is desirable to minimize or eliminate phospholipase C hydrolysis of phospholipids, and to permit the use of phospholipids in drug-delivery systems.

One technique of employing phospholipids, such as synthetic lecithins, to prepare controlled-release pharmaceutical compositions, is described in U.S. Pat. No. 4,016,100, issued Apr. 5, 1977, hereby incorporated by reference. This method comprises the steps of: dispersing a phospholipid uniformly in water to give an aqueous phospholipid dispersion having lipid spherules; adding a medicament to the aqueous phospholipid dispersion to form a medicament dispersion; freezing said medicament dispersion, thereby entrapping the medicament in the lipid spherules; and then thawing the frozen dispersion to give an aqueous suspension of the medicament entrapped in said lipid spherules. In such techniques, a wide variety of pharmaceutical compounds may be used, including bronchodilators, vitamins, medicants, hormones, antibiotics, including water-insoluble and water-soluble compounds. However, the use of the phospholipids described is not wholly satisfactory, due to the rapid hydrolysis of such phospholipids on oral administration of the encapsulated compounds.

SUMMARY OF THE INVENTION

My invention relates to a method for the preparation of controlled-release pharmaceutical compositions and to the controlled-release compositions so prepared. In particular, my invention concerns the preparation of controlled-release pharmaceutical compositions with synthetic phospholipids, which phospholipids are characterized by decreased rates of phospholipase C hydrolysis, and to the controlled-release compounds so prepared.

I have found that the use of synthetic phospholipids, in which the polar moiety of the phosphatidyl choline head group is altered, provides synthetic phospholipids having a decreased rate of phospholipase C hydrolysis which permits the use of such phospholipids as surfactants for controlled-release purposes.

The use of such phospholipids considerably enhances the ability of various drug compounds to be administered orally. It has been discovered that such phospholipids, with decreased or eliminated polar-head-group hydrolysis, permit the phospholipids to be resistant to hydrolysis in the stomach, and, therefore, such phospholipids and encapsulated compounds are able to be absorbed by the gut or intestinal system. Such phospholipids, with altered head groups, would include those phospholipids that have a fatty-acid ester linkage, or exist in the gel state at the temperature of use, such as about 37° C., or have incorporated therein high amounts of cholesterol, cholesterol derivatives or similar compounds; for example, with cholesterol greater than 35 mole percent (see J.A.F. Op Den Kamp et al., supra).

The phospholipids useful in my method are surfactants which form micelles in self-association (vesicles), or with other lipids (microemulsions), and which phospholipids are resistant to enzymatic hydrolysis. Synthetic phosphonium, sulfonium, and particularly quaternary-ammonium phospholipids, as described in my copending applications (supra), and related compounds with different polar-head groups, are useful in my method.

These synthetic phospholipids are useful in encapsulating various drugs, such as insulin and antitumor drugs, for oral administration; that is, drugs which normally would be hydrolyzed in the stomach on oral administration. The encapsulated controlled-release drug compositions, with hydrolysis eliminated or minimized, would not be released in the stomach by the hydrolysis of the encapsulating phospholipids, but would be permitted to be absorbed by the gut for eventual localization in the bloodstream or other tissues in the body, wherein the released drug could assert its desired effect.

Many drugs that are orally administered are usually hydrolyzed by enzymes in the stomach, but usually a high enough concentration of the drug is used, so that enough of the drug is able to pass through the stomach and be absorbed by the gut, and eventually enter into the bloodstream. Many other drugs, such as antitumor agents or insulin, have to be injected directly into the bloodstream, since these drugs would be inactivated totally in the stomach. However, by encapsulating these drugs in my phospholipid structures, it is possible to prevent the drug hydrolysis in the stomach. My drug-delivery system requires that the encapsulating lipid structure, itself, not be hydrolyzed, thereby releasing its contents. Therefore, my lipid drug carrier permits oral administration of many drugs that are now injected, and also allows a greater effectiveness of drugs that are presently given orally.

The phospholipids useful in my method comprise phosphatidyl compounds, wherein the sulfonium, phosphonium and quaternary-ammonium polar-head moiety of such compounds has been modified by hydrocarbon groups, particularly alkyl groups, over that of natural or synthetic lecithin or the phosphonium or sulfonium lecithin derivatives. Phosphatidyl compounds, wherein the phosphatidyl portion contains ester groups; for example, $C_{14}$ to $C_{20}$ fatty-acid groups (the same or different), are useful, such as dihydrocarbon phosphatidyl alkyl N-trialkyl ammonium hydroxide, wherein the hydrocarbon; for example, the alkyl group, is typically $C_1$ to $C_4$, with the alkyl group between the nitrogen and phosphorous atoms ranging, for example, from $C_1$ to $C_{10}$, except that natural or synthetic lecithin is excluded from these useful compounds.

Similar phosphonium and sulfonium phospholipids are useful where the sulfur atom or phosphorous atom replaces the quaternary-ammonium atom.

The phosphatidyl choline compounds useful may be represented by the structural formula:

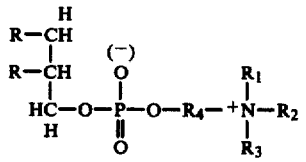

wherein R is a fatty radical, such as a radical derived from fatty acids or alcohols, the same or different, but preferably a $C_{14}$ to $C_{20}$ fatty-acid ester radical, such as myristoyl, stearoyl, palmitoyl, oleatoyl, linoleatoyl, or a natural material like egg yolk, soybeans, etc.; $R_1$, $R_2$ and $R_3$ are alkyl radicals, the same or different, typically $C_1$ to $C_4$ radicals, such as methyl, ethyl, propyl and butyl; and $R_4$ is an methylene radical, typically a $C_1$ to $C_{10}$ radical, preferably a $C_1$ to $C_4$ radical, such as dimethylene, trimethylene, tetramethylene, hexamethylene, octamethylene, nonamethylene, etc. In the above formula, $R_4$ cannot be dimethylene while $R_1$, $R_2$ and $R_3$ are methyl radicals.

Where sulfur or phosphorous atoms replace the quaternary nitrogen, corresponding adjustment is made in the number of radical groups in accordance with the valence of the new atom. Preferred compounds are those where $R_1$, $R_2$ and $R_3$ are all the same radical, particularly methyl or ethyl, and $R_4$ is a different and preferably longer radical; for example, tetramethylene or trimethylene, and R is a fatty-acid radical.

In my method, the synthetic phospholipid is dispersed in water with the pharmaceutical compound whose release is to be controlled (other additives and surfactants added, if desired) to form a dispersion or emulsion, and, thereafter, the emulsion is coagulated, such as by precipitation, frozen, coagulants are added, the temperature or pH is changed, or other methods used to entrap and encapsulate the pharmaceutical compound within the phospholipid, and the encapsulated material is recovered for use or administration. The controlled-release material may be used alone or with other materials. One technique, in preparing controlled release with my phospholipid composition, is set forth in U.S. Pat. No. 4,016,100, supra.

For the purpose of illustration only, my method will be described in connection with the use of certain preferred synthetic phospholipids, as set forth in the examples; however, it is recognized that other phospholipids and other methods of preparation may be used, which are all within the spirit and scope of my invention.

BRIEF DESCRIPTION OF THE DRAWING

The drawing is a graphical representation of comparative tests of the hydrolysis rate of various synthetic phospholipids, comparing percent hydrolysis of the phospholipid with the time and hours.

DESCRIPTION OF THE EMBODIMENTS

Tests to determine the comparative rates of phospholipase C hydrolysis of my modified phospholipids and phosphatidyl choline were carried out as follows: 18 mg dimyristoyl derivatives of each phospholipid compound, identified in Table I, A-F, was lyophilized from benzene. To the dried lipid was added 1 ml of 0.1M KCl, 10mM $CaCl_2$ (pH 7.4) and 2 mg of phospholipase C. Then 2 ml of diethyl ether was added to each sample. The solution so prepared is a synthetic, aqueous, acidic composition of a standardized assay mixture. The solutions were shaken at 24° C., and at various time points, aliquots were taken from the aqueous phase. The aliquots were assayed over a time period for the appearance of phosphorylcholine in the aqueous phase.

The phospholipids tested are set forth in Table I.

TABLE I

| Identification | Compound |
|---|---|
| A. | Dimyristoyl phosphatidyl choline |
| B. | Dimyristoyl phosphatidyl ethyl-N—dimethyl, propyl ammonium hydroxide |
| C. | Dimyristoyl phosphatidyl ethyl-N—dimethyl, |

TABLE I-continued

| Identification | Compound |
|---|---|
| | ethyl ammonium hydroxide |
| D. | Dimyristoyl phosphatidyl propyl-N—trimethyl ammonium hydroxide |
| E. | Dimyristoyl phosphatidyl butyl-N—trimethyl ammonium hydroxide |
| F. | Dimyristoyl phosphatidyl propyl-N—triethyl ammonium hydroxide |

The test results are shown in Table II and graphically in the drawing, wherein the percent hydrolysis in the composition was plotted against the time in hours in the mixture.

TABLE II

| Compound | Data Results Time in Hours | % Hydrolysis |
|---|---|---|
| A | ½ | 58 |
| | 1 | 84 |
| | 2¼ | 100 |
| | 4 | 100 |
| B | ½ | 13 |
| | 1 | 53 |
| | 2¼ | 97 |
| | 4 | 100 |
| C | 1 | 25 |
| | 2¼ | 55 |
| | 4 | 100 |
| D | ½ | 2 |
| | 1 | 5 |
| | 2¼ | 18 |
| | 4 | 100 |
| E & F | 1 | 2 |
| | 2¼ | 3 |
| | 4 | 5 |

Dimyristoyl phosphatidyl choline was the most rapidly hydrolyzed phospholipid, whereas my modified phospholipid compounds were retarded in their enzymatic hydrolysis. In fact, two of the compounds tested, dimyristoyl phosphatidyl propyl-N-triethyl ammonium hydroxide (F) and dimyristoyl phosphatidyl butyl-N-trimethyl ammonium hydroxide (E), demonstrated little hydrolysis by phospholipase C.

Therefore, the synthetic modifications placed in the polar-head group structure of phosphatidyl choline have resulted in unexpected and surprising altered resistance to phospholipase C hydrolysis. My phospholipid compounds employed as surfactants and encapsulation agents for drugs, such as insulin, should not be hydrolyzed in the stomach on oral administration, assuming that suitable precautions to prevent phospholipase A hydrolysis have been taken.

A controlled-release pharmaceutical composition is prepared by dispersing the phospholipids E and F in water using a blender; for example, an amount of 0.001 to 0.2 g/ml, and then adding and dispersing a drug, subject to phospholipase C enzymatic hydrolysis, such as insulin, to the phospholipid dispersion; for example in an amount of 0.01 to 1.0 grams per gram of the phospholipid used. The dispersion is then frozen; for example, to below −5° C., and then is permitted to thaw to 15° to 40° C. The thawed aqueous suspension is then separated; for example, by centrifuging, to separate and recover the entrapped drug. The recovered, entrapped phospholipid insulin may be employed as a controlled-release drug-delivery system on oral administration, since the drug is prevented from enzymatic hydrolysis by the employment of the phospholipid delivery agent, which is resistant to enzymatic hydrolysis by phospholipase C, thereby permitting the drug to pass through the stomach and into the gut of the patient.

There are a variety of techniques which may be employed to encapsulate drugs employing my phospholipids. One preferable technique, which produces small-size particles for oral absorption (for example, less than 500-Angstrom particles), comprises the sonication of the drug and the phospholipid compounds together, followed by separation of the sonicated encapsulated drug within the particles from the nonencapsulated drug by techniques such as gel-partition column chromatography in U.S. Pat. No. 4,016,100. The method described, while satisfactory, is not wholly desirable in that the particle size obtained is often too large for efficient absorption of the encapsulated drug.

My invention has been described in connection with the preparation of controlled-release drug compositions; however, where desired, my enzymatic-resistant phospholipids may be used alone for direct oral administration for use or application in the intestinal tract, where beneficial or desired.

What I claim is:

1. In a method for preparing a controlled-release pharmaceutical composition for oral administration, the method which comprises: forming an aqueous emulsion of phospholipid encapsulating agent with the pharmaceutical compound whose release is to be controlled; coagulating the emulsion to entrap the pharmaceutical compound within the phospholipid agent; and recovering the pharmaceutical composition as prepared, the improvement which comprises:

employing as the phospholipid encapsulating agent a synthetic fatty-acid phosphatidyl [$C_1$–$C_{10}$ alkyl-N-$C_1$–$C_4$ trialkyl] quaternary-ammonium hydroxide compound[, with the proviso that the alkyl of the alkyl-N group is not an ethyl group when the alkyl groups of the N-trialkyl radicals are methyl groups] *represented by the structural formula:*

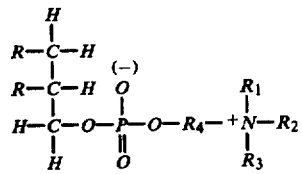

*wherein $R_4$ is a $C_1$–$C_{10}$ methylene radical and $R_1$, $R_2$ and $R_3$ are $C_1$–$C_4$ alkyl radicals, with the proviso that $R_1$, $R_2$ and $R_3$ at the same time are not all methyl radicals and wherein R is a fatty-acid radical,* and which phosphatidyl quaternary-ammonium compound is resistant to enzymatic hydrolysis of phospholipase C.

2. The method of claim 1 wherein the [fatty acid] *fatty-acid radical* is a $C_{14}$ to $C_{20}$ fatty-acid radical.

3. The method of claim 1 wherein [the alkyl-N of the quaternary-ammonium compound is butyl-N or propyl-N, and] the [trialkyl groups] $R_1$, $R_2$ *and* $R_3$ *alkyl radicals* are all the same alkyl [group] *radical.*

4. The method of claim 3 wherein the [trialkyl groups] $R_1$, $R_2$ *and* $R_3$ *alkyl radicals* are methyl or ethyl [groups] *radicals.*

5. The method of claim 1 wherein the quaternary-ammonium compound is selected from the group consisting of: dimyristoyl phosphatidyl ethyl-N-dimethyl, propyl ammonium hydroxide; *and* dimyristoyl phosphatidyl ethyl-N-dimethyl, ethyl ammonium hydroxide[; dimyristoyl phosphatidyl propyl-N-trimethyl ammonium hydroxide; dimyristoyl phosphatidyl butyl-N-trimethyl ammonium hydroxide; and dimyristoyl phosphatidyl propyl-N-triethyl ammonium hydroxide].

6. The method of claim 1 wherein the pharmaceutical compound is insulin.

7. The controlled-release composition prepared by the method of claim 6.

8. The method of claim 1 wherein the encapsulated pharmaceutical compound is enzymatically hydrolyzed by phospholipase C in the stomach.

9. The controlled-release pharmaceutical composition prepared by the method of claim 1.

10. The method of claim 1 which comprises: sonification of the pharmaceutical compound and the synthetic phospholipid compound together to encapsulate the pharmaceutical compound.

* * * * *